United States Patent [19]

Frazee et al.

[11] Patent Number: 5,908,407
[45] Date of Patent: Jun. 1, 1999

[54] RETROPERFUSION CATHETER APPARATUS AND METHOD

[75] Inventors: John G. Frazee, Toluca Lake; David C. Cornett, Newport Beach; Scott M. Evans, Santa Ana, all of Calif.

[73] Assignee: Neuroperfusion, Inc., Irvine, Calif.

[21] Appl. No.: 08/900,967

[22] Filed: Jul. 25, 1997

[51] Int. Cl.[6] .................................................. A61M 29/00
[52] U.S. Cl. ........................ 604/101; 604/49; 604/53; 604/65; 604/99; 606/194
[58] Field of Search ................................ 604/101, 65–67, 604/27, 30, 31, 49–53, 280, 96–100; 606/192, 194; 600/16, 17, 18

[56] References Cited

U.S. PATENT DOCUMENTS

| | | |
|---|---|---|
| 4,573,966 | 3/1986 | Weikl et al. . |
| 4,610,662 | 9/1986 | Weikl et al. . |
| 4,636,195 | 1/1987 | Wolinsky . |
| 4,696,668 | 9/1987 | Wilcox . |
| 4,705,502 | 11/1987 | Patel . |
| 4,705,507 | 11/1987 | Boyles . |
| 4,771,777 | 9/1988 | Horzewski et al. . |
| 4,781,677 | 11/1988 | Wilcox . |
| 4,824,436 | 4/1989 | Wolinsky . |
| 4,930,496 | 6/1990 | Bosley, Jr. . |
| 4,943,277 | 7/1990 | Bolling . |
| 4,976,692 | 12/1990 | Atad . |
| 5,024,658 | 6/1991 | Kozlov et al. . |
| 5,059,178 | 10/1991 | Ya . |
| 5,090,960 | 2/1992 | Michael . |
| 5,135,484 | 8/1992 | Wright . |
| 5,163,905 | 11/1992 | Michael . |
| 5,213,577 | 5/1993 | Kratzer . |
| 5,222,941 | 6/1993 | Michael . |
| 5,256,141 | 10/1993 | Gencheff et al. . |
| 5,279,546 | 1/1994 | Mische et al. . |
| 5,314,409 | 5/1994 | Sarosiek et al. . |
| 5,320,604 | 6/1994 | Walker et al. . |
| 5,342,306 | 8/1994 | Michael . |
| 5,380,284 | 1/1995 | Michael . |
| 5,397,307 | 3/1995 | Goodin . |
| 5,419,763 | 5/1995 | Hildebrand . |
| 5,423,744 | 6/1995 | Gencheff et al. . |
| 5,460,610 | 10/1995 | Michael . |
| 5,478,309 | 12/1995 | Sweezer et al. ................... 604/101 X |
| 5,484,412 | 1/1996 | Pierpont ............................. 601/101 |
| 5,501,667 | 3/1996 | Verdvin, Jr. ..................... 606/194 X |
| 5,505,701 | 4/1996 | Anaya Fernandez de Lomana . |
| 5,505,702 | 4/1996 | Arney ..................................... 604/101 |
| 5,509,897 | 4/1996 | Twardowski et al. . |
| 5,514,092 | 5/1996 | Forman et al. . |
| 5,674,198 | 10/1997 | Leone . |
| 5,728,068 | 3/1998 | Leone, Jr. ............................ 604/101 |
| 5,762,624 | 6/1998 | Peters .............................. 606/194 X |

*Primary Examiner*—John D. Yasko
*Attorney, Agent, or Firm*—Myers, Dawes & Andras

[57] ABSTRACT

A catheter for retroprofusing a venous junction formed by first, second and third veins, includes an elongate tube having a plurality of channels including a through-lumen extending between a proximal end and a distal end. A proximal balloon is inflatable to partially occlude the third vein, while a distal balloon is inflatable to partially occlude the second vein. An operative region of the catheter between the first and second balloons is adapted to pressurize the venous junction with arterial blood to produce retrograde blood flow in the first vein.

12 Claims, 3 Drawing Sheets

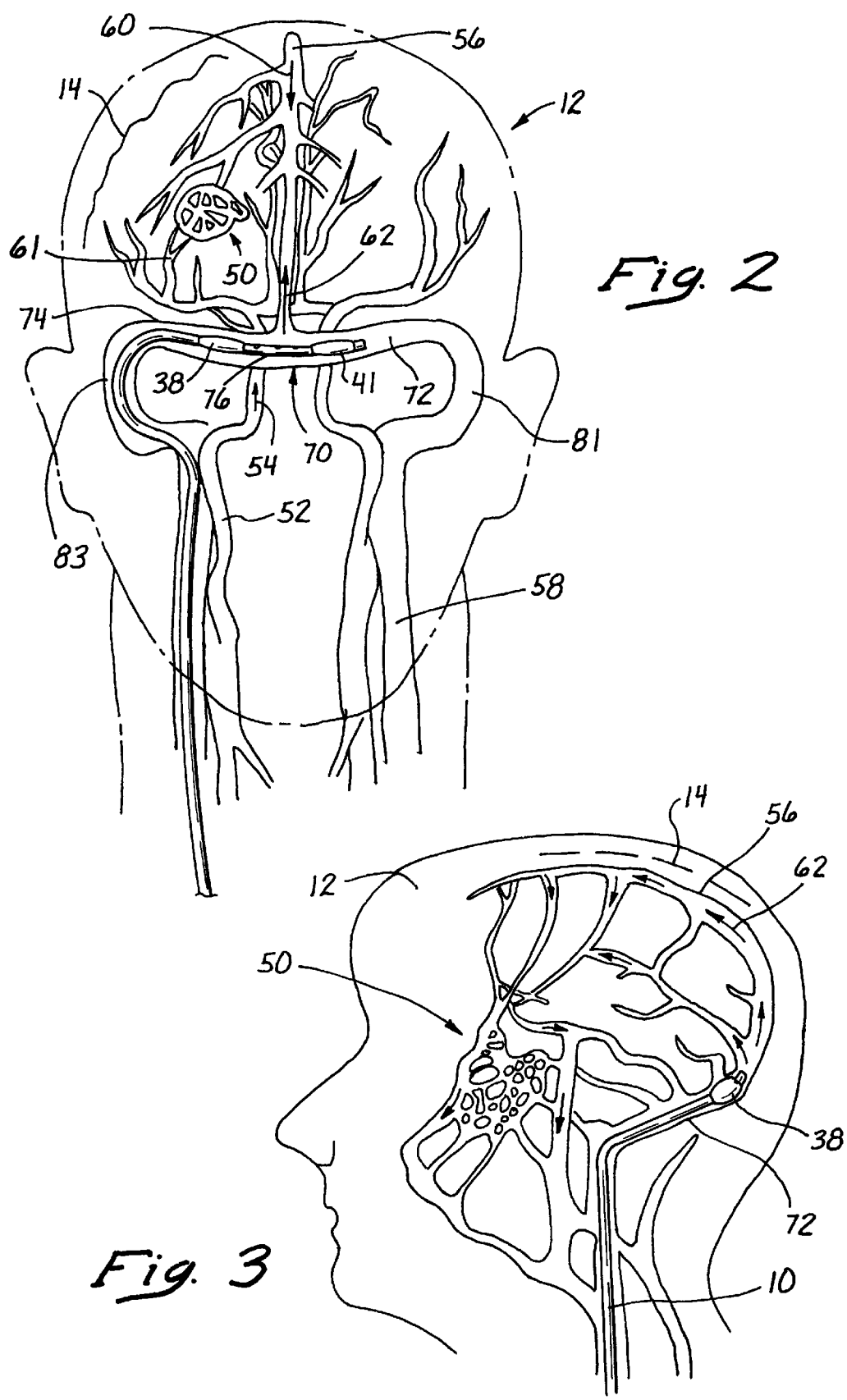

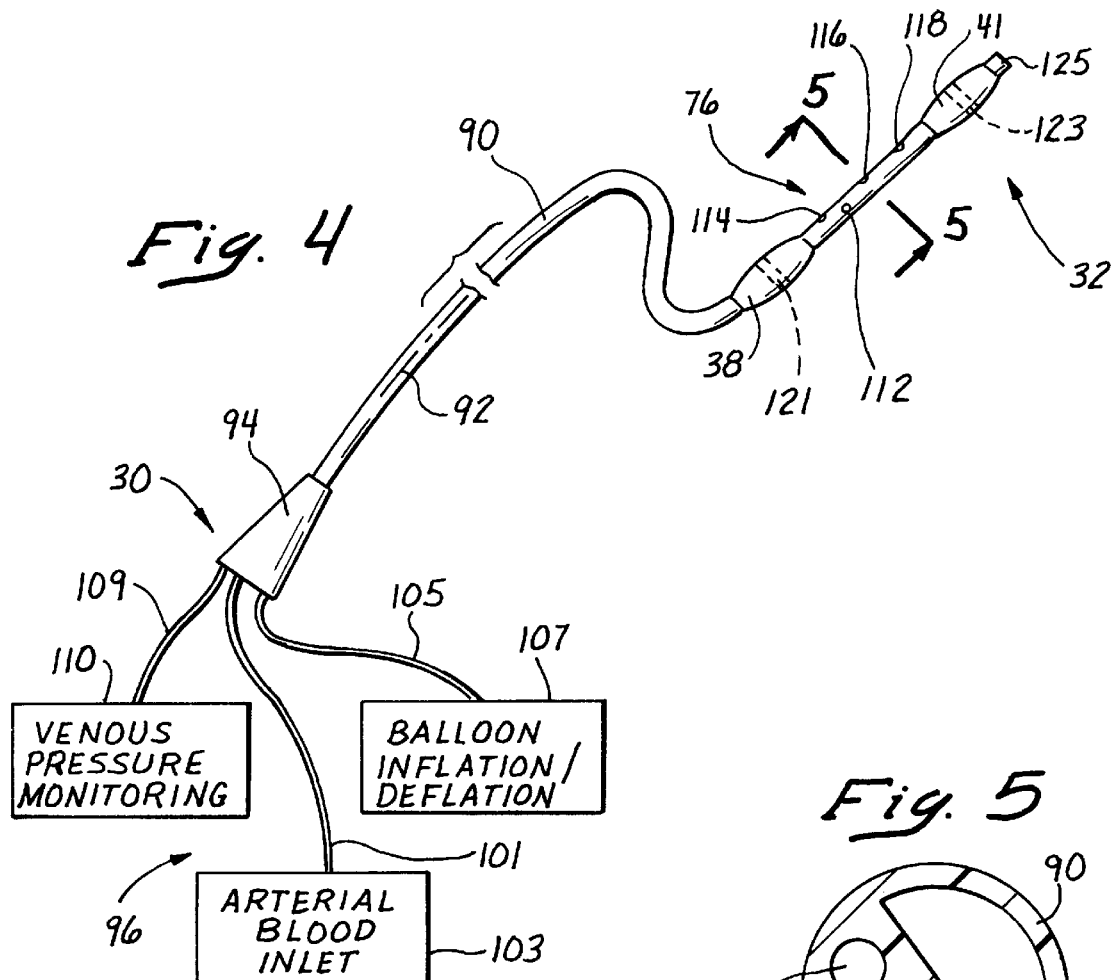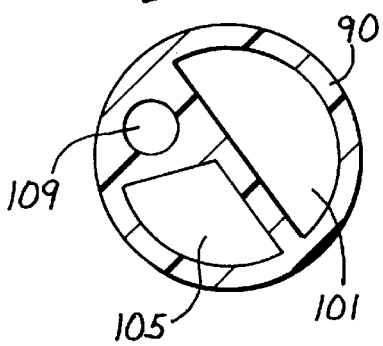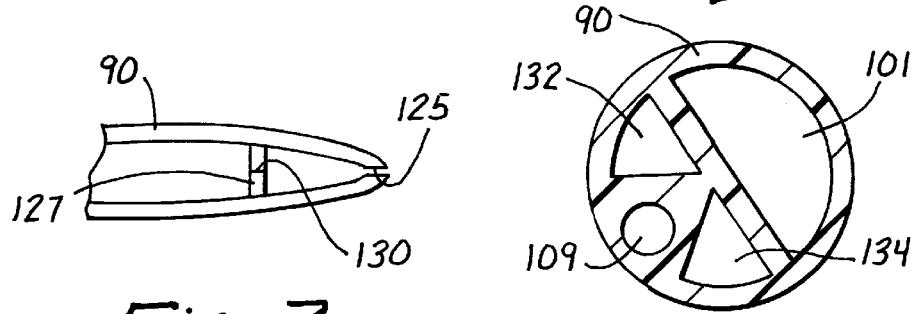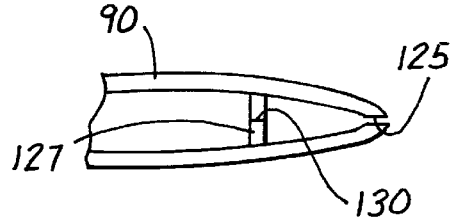

RETROPERFUSION CATHETER APPARATUS AND METHOD

BACKGROUND OF THE INVENTION

1. Field of the Invention

This invention relates generally to retroperfusion catheters and methods, and more specifically to such apparatus and methods particularly adapted for use in perfusing ischemic brain tissue.

2. Discussion of the Prior Art

Tissue of the human body is maintained viable with oxygen which is delivered to the body in blood which is pumped through a labyrinth of vessels by the heart. Initially, the blood is pumped into arteries which direct it into capillary beds throughout the tissue. Oxygen is removed from the blood by the tissue surrounding these capillary beds.

The deoxygenated blood is collected from the capillary beds and returned to the heart through veins. The blood is then reoxygenated in the lungs and pumped back out through the arteries by the heart.

In the head, the oxygenated blood is carried by the carotid and vertebral arteries which ultimately deliver the oxygenated blood to capillary beds in the brain. The deoxygenated blood is collected from the capillary beds and returned through the jugular veins to the heart.

Stroke most often occurs in a patient when an embolus is carried into one of the arteries in the head. In these narrowing arteries, the embolus becomes lodged, blocking the flow of oxygenated blood to the downstream capillary beds. Without the life-sustaining oxygen and other essential blood components, these capillary beds become ischemic and the brain tissue degenerates, causing the stroke.

For decades, medical investigators have unsuccessfully sought to develop an early treatment for ischemic brain stroke. It has been appreciated that the more quickly one addresses the lack of oxygen in the brain, the more likely it is that the degeneration of the tissue can be prevented and the stroke avoided.

A system and method of cerebral retroperfusion is disclosed and claimed in applicant's copending application, Ser. No. 08/757,303, filed on Nov. 27, 1996, now U.S. Pat. No. 5,794,629 and entitled, "Method for Treating Ischemic Brain Stroke." This application is incorporated herein by reference. In this document, applicant discloses a system involving multiple catheters which are used to at least partially occlude the jugular veins while continuously pumping arterial blood into one or both of the cerebral sinuses. The multiple catheters disclosed for use in this system have required separate placement and operation in order to achieve both the occlusion and retroperfusion aspects of the procedure. The retroperfusion by these catheters has been achieved by way of a through-lumen which exits the distal tip of at least one of the catheters. This through-lumen is readily available as its secondary purpose is to facilitate placement of the catheter over a guidewire. Once the guidewire is removed, the through-lumen can be used to facilitate perfusion.

SUMMARY OF THE INVENTION

In accordance with the present invention, these deficiencies of the prior art are overcome with a single, dual-balloon catheter which is inserted into one of the jugular veins and positioned across a venous junction. One such junction is formed by the superior sagittal sinus and the left and right transverse sinuses.

In a three-lumen catheter of the present invention, an inflation lumen is provided to inflate the balloons to at least partially occlude the associated transverse sinuses. A perfusion lumen exits the catheter laterally between the two balloons and provides a flow of oxygenated blood to the venous junction. Although antegrade, or normal, blood flow in the superior sagittal sinus is into the junction, the pressure of the perfused blood is elevated, resulting in retroperfusion or retrograde flow upwardly into the ischemic capillary bed. In this manner, oxygen and other essential blood components are carried to the ischemic capillary bed, maintaining that tissue viable so that the blockage or embolism on the other side of the capillary bed can be addressed. In this manner, the effect of a stroke can be immediately addressed and minimized.

In one aspect of the invention, a catheter for retroperfusing a venous junction defined by a first vein providing normal blood flow into the junction and a second and third vein each providing normal blood flow away from the junction, includes an elongate tube having an axis extending between a proximal end and a distal end. Portions of the tube define a plurality of channels including a through-lumen. A first balloon is disposed in proximity to the distal end of the tube and is adapted to partially occlude the third vein. A second balloon is disposed in proximity to the first balloon and adapted to partially occlude the second vein, with the venous junction disposed between the first balloon and the second balloon. A perfusion lumen, included among the channels, has multiple outlet ports between the first and second balloons, and is adapted to receive arterial blood under pressure in order to induce retrograde blood flow in the first vein. A pressure lumen included among the channels provides fluid communication between a pressure transducer and the venous junction.

In a further aspect of the invention, a catheter combination for retroperfusing a venous junction defined by a first vein providing normal blood flow into the junction and a second and third vein each providing normal blood flow away from the junction, comprises a catheter having an axis extending between a proximal end and a distal end. Portions of the catheter define a plurality of channels including a through-lumen. First and second balloons are disposed at the distal end of the catheter and define an operative region of the catheter. When the catheter is properly disposed, the first balloon is positioned in the third vein and the second balloon is positioned in the second vein, with the operative region in proximity to the venous junction. A retroperfusion lumen is included among the channels and adapted to receive arterial blood flow from a blood pump connected to the proximal end of the catheter. The pump has properties for pressurizing the flow of arterial blood at the venous junction so as to produce a retrograde flow in the first vein. An inflator communicating with an inflation lumen provides fluid under pressure for the inflation and deflation of the balloons in order to control the degree of occlusion of the their respective veins. In response to the indication of a pressure transducer in a pressure lumen of the catheter, at least one of the balloons can be inflated or deflated in order to adjust the antegrade flow of blood in the associated vein.

An associated method includes the steps of introducing the catheter into the second vein and positioning the catheter with the first balloon disposed in the third vein, the second balloon disposed in the second vein, and the operative region of the catheter disposed in proximity to the venous junction. The method also includes the steps of pressurizing the perfusion lumen with arterial blood to induce retrograde flow in the first vein, and pressurizing an inflation lumen to inflate at least the first balloon in order to control the antegrade blood flow from the venous junction. This catheter and pump can also be used for the infusion of certain neuroprotection pharmacological agents in conjunction with the arterial blood flow.

These and other features and advantages of the invention will become more apparent with a discussion of preferred embodiments and reference to the associated drawings.

DESCRIPTION OF THE DRAWINGS

FIG. 2 is a side view of the head of the patient showing the brain, a carotid artery, a capillary bed, and a venous junction;

FIG. 3 is a front side view of the head, brain, carotid artery, capillary bed and venous junction illustrated in FIG. 2;

FIG. 4 is a schematic view of a preferred embodiment of the catheter of the present invention;

FIG. 5 is a radial cross section view taken along lines 5—5 of FIG. 4;

FIG. 6 is a radial cross section view similar to FIG. 5 and illustrating a further embodiment of the invention; and FIG. 7 is an axial cross section view of the distal end of the catheter illustrating a septum valve.

DESCRIPTION OF PREFERRED EMBODIMENTS AND BEST MODE OF THE INVENTION

Figure 1:
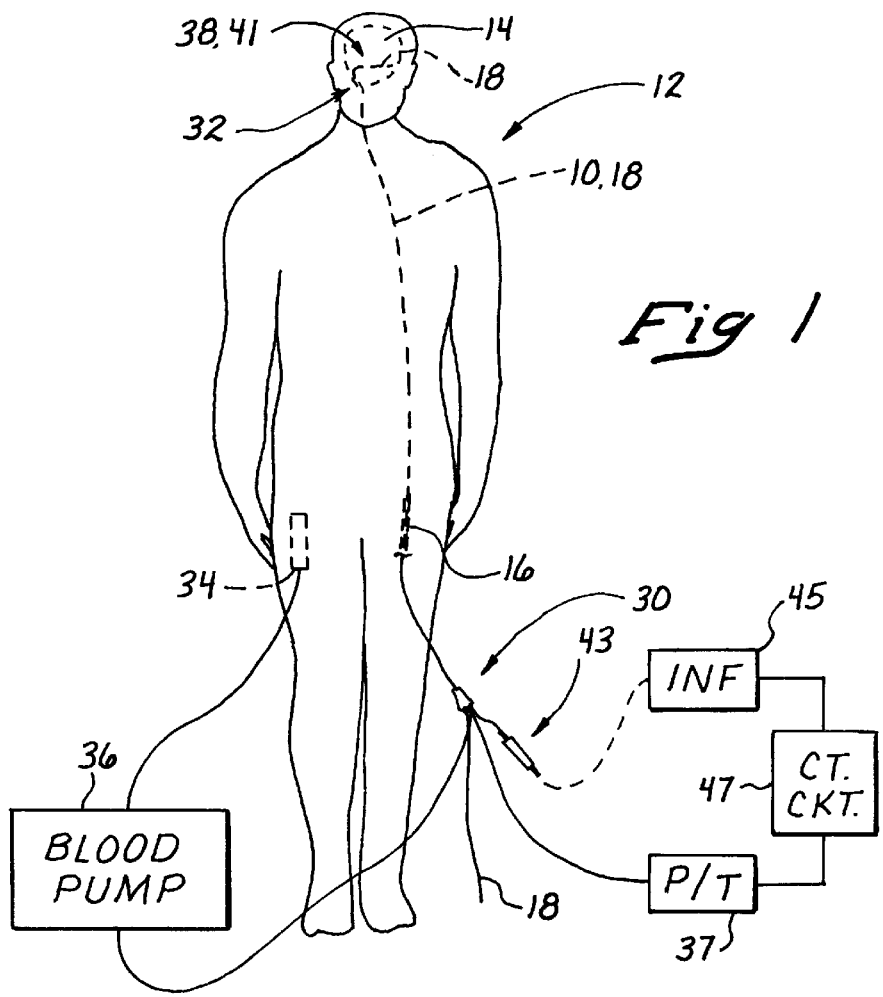
FIG. 1 is a schematic view of a patient and a catheter of the present invention operatively positioned to retroperfuse ischemic brain tissue.

A catheter is illustrated in FIG. 1 and designated generally by the reference numeral 10. The catheter 10, as illustrated, is operatively disposed in a patient 12 having ischemic tissue in his brain 14. The catheter 10 is inserted in the femoral vein 16 over a guidewire 18 and passed through the chest of the patient 12 into the brain 14. When operatively disposed, the catheter 10 has a proximal end 30 which is exposed at the femoral vein 16, and a distal end 32 which is operatively positioned in the brain 14.

Oxygenated blood is taken from a femoral artery 34 by a blood pump 36 and introduced into the proximal end 30 of the catheter 10. This oxygenated blood delivered to the brain 14 under pressure in order to produce a retrograde blood flow in the venous side of the brain. Thus, oxygen and other essential blood components are carried by the perfused blood to the ischemic brain tissue. This not only maintains the viability of that tissue but provides precious time during which the cause of the ischemia can be addressed.

The pressure of the perfusion blood in the brain 14 can be monitored by a pressure transducer 37 connected to the proximal end 30 of the catheter 10. A pair of occlusion balloons 38 and 41 at the distal end 32 of the catheter 10, are inflatable and deflatable by an inflator which in its simplest form may comprise a syringe 43. Alternatively, the inflator may comprise a variable pressure source 45 connected to the proximal end 30 of the catheter 10.

A simplified anatomy of the brain 14 is illustrated in FIG. 2 where a single capillary bed is designated by the reference numeral 50. This bed 50 is normally fed with oxygenated blood through a carotid artery 52 having antegrade or normal blood flow in the direction illustrated by an arrow 54. This oxygenated blood in the carotid artery 52 is fed into the labyrinth of small capillaries in the bed 50 which carries the oxygen to feed the cells of the tissue. After the oxygen is removed from the blood in the capillary bed 50, the deoxygenated blood is fed into the venous side of the bed, for example into the superior sagittal sinus 56 and ultimately into the jugular vein 58. The antegrade or normal direction or blood flow in the sagittal sinus 56 is indicated by the arrow 60.

Stroke most often occurs in the patient 12 when a blood clot or embolus 61 is carried by the antegrade blood flow in the carotid artery 52 into one of the narrowing cerebral arteries leading to the capillary bed 50. This embolus 61 blocks the artery so that the oxygenated blood which would normally maintain the viability of the bed 50 is blocked. Without oxygen from this blood, the tissue surrounding the bed 50 becomes ischemic and begins to irreversibly degrade.

As noted, it is the purpose of the catheter 10 to introduce oxygenated blood under pressure into the superior sagittal sinus 56 in order to produce a retrograde flow (opposite to normal direction) into the venous side of the capillary bed 50. This retrograde flow is illustrated to be in the direction of an arrow 62 which is opposite in direction to the antegrade flow represented by the arrow 60. The retrograde blood flows through the bed 50 into other portions of the venous system, before it collects in the jugular vein 58.

A preferred placement of the catheter 10 with respect to the superior sagittal sinus 56 is also illustrated in FIG. 2. From this view, it can be seen that the superior sagittal sinus 56 forms a venous junction 70 where it meets a left transverse sinus 72 and a right transverse sinus 74. From this view, it will also be appreciated that the balloons 38 and 41 of the catheter 10 are axially spaced and define an operative region 76. The catheter 10 can be inserted over the guidewire 18 through either a left sigmoid sinus 81, or as illustrated through a right sigmoid sinus 83. When inserted on the right side of the brain 14, the distal balloon 41 is preferably located in the left transverse sinus 72. The more proximal balloon 38 is operatively disposed in the right transverse sinus 74. This leaves the operative region 76 of the catheter 10 disposed in proximity to the junction 70. The oxygenated blood to be perfused is introduced through the catheter 10 into the operative region 76 and through the wall of the catheter 10 into the superior sagittal sinus 56 to produce the retrograde flow represented by the arrow 62.

Given this general description of the surgical environment, and further reference to FIGS. 3–5, one can more easily understand the advantageous structure associated with catheter 10. In a preferred embodiment, the catheter 10 includes an elongate tube 90 having an axis 92 which extends between the proximal end 30 and distal end 32. The tube 90 includes a plurality of channels 92, more commonly referred to as lumens, which extend at least partially through the tube 90. At the proximal end 30, these channels 92 are connected through a hub 94 to respective connectors 96.

For example, as illustrated in FIG. 6, catheter 10 may have a through-lumen 101 which extends entirely through the tube 90 from an associate connector 103 through to the tip of the catheter 10 at the distal end 32. An inflation lumen 105 is in communication with a connector 107 and exits the tube 90 beneath the balloons 38 and 41. Thus, air or some other fluid may be introduced into the connector 107 by the syringe 43 or variable pressure source 45 (FIG. 1) to inflate the balloons 38 and 41.

A further lumen 109 extends from a connector 110 and exits the tube 90 through a port 112 in the operative region 42 of the catheter 10. This pressure lumen 109 permits fluid pressure in the vicinity of the operative region 42 to be monitored through a fluid column in the lumen 109.

As discussed in greater detail below, the through lumen 101 in this embodiment can also function as a perfusion lumen which extends from the connector 103 through the tube 90 and exits the catheter 10 through a plurality of ports 114, 116 and 118 in the operative region 76. This perfusion lumen 101 permits the oxygenated blood to be introduced into the connector 103 to exit the catheter 10 through the ports 114–118 in the operative region 76. Additional structure may be provided in the form of radiopaque markers 121, 123 which in this embodiment are disposed beneath the balloons 38 and 41, respectively. These markers 121, 123 facilitate operative placement of the catheter 10 in a manner well known in the art.

As noted, the through-lumen 101 also functions as a perfusion lumen in this embodiment. In order to accomplish both of these functions, the lumen 101 is not only provided with the perfusion ports 114, 116 and 118, but also provided with a hole 125 at the distal end 32 of the catheter 10. While this hole 125 is particularly adapted to facilitate insertion over the guidewire 18, it must be closed or at least partially blocked in order to facilitate perfusion through the ports 114–118.

In a preferred embodiment, the hole 125 is at least partially blocked by a septum valve 127 having a slit 130 which extends therethrough. When the catheter 10 is being inserted, the guidewire 18 extends through the hole 125 and the slit 130 in the septum valve 127. Once the catheter 10 is operatively positioned, the guidewire 18 is removed and the slit 130 closes substantially blocking the hole 125. This facilitates perfusion of the oxygenated blood through the ports 114–118 in the operative region 42.

In a further embodiment of the invention, the number of lumens or channels 92 in the tube 90 may be increased, for example as illustrated in FIG. 6. Although this embodiment includes the through-lumen 101 which also functions as a perfusion lumen, as well as the pressure lumen 109, it also includes separate inflation lumen 132 and 134 which are provided to independently inflate the respectively balloons 38 and 41.

Figure 8:
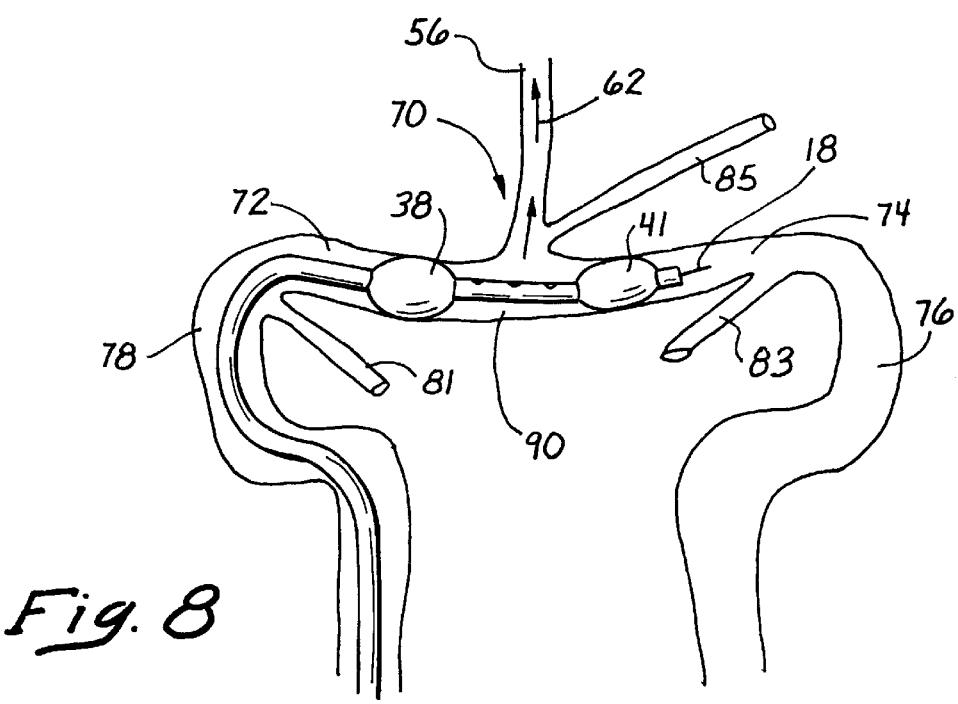
FIG. 8 is a front side view of a venous junction showing a catheter of the present invention operatively disposed to perfuse the superior sagittal sinus.

Given this structure for a preferred embodiment, operation of the catheter 10 within the cerebral veins will be more easily understood, particularly with reference to the detail of FIG. 8. From this view, it will be seen that other veins of interest in the vicinity of the junction 70 include the superior petrosal sinus 81 which is in fluid communication with the right sigmoid sinus 78 and the vein 83 which is in fluid communication with the left transverse sinus 72. A straight sinus 85 is connected to the superior sagittal sinus 56 in close proximity to the junction 70. In a manner commonly used for the placement of catheters, the procedure of the present invention begins with the introduction of the guidewire 18. A percutaneous puncture is made in the femoral vein 16 in the manner discussed with reference to FIG. 1, and the distal end 32 of the guidewire 18 is urged along the desired venous path to its final operative position illustrated in FIG. 8. In this position, the guidewire 18 extends through the right sigmoid sinus 78, the right transverse sinus 72, the junction 70, and into the left transverse sinus 74. Placement of the guidewire 18 is facilitated by its nimble structure which enables the guidewire 18 to be moved along a circuitous path.

With the guidewire 18 properly positioned, the distal end 32 of the catheter 10 is threaded over the proximal end of the guidewire 18. With the guidewire 18 dictating the preferred path, the catheter 10 can merely be pushed along the guidewire 18 until it reaches the operative position illustrated in FIG. 8. In this position, the distal balloon 41 is disposed in the left transverse sinus 74 and preferably between the vein 83 and the straight sinus 85. The more proximal balloon 38 is disposed in the right transverse sinus 72 between the superior petrosal sinus 81 and the junction 70. In a preferred embodiment, the balloons 38 and 41 are separated by a distance of about 3–6 centimeters.

When operatively disposed, the balloons 38 and 41 can be inflated to at least partially occlude the respective right and left transverse sinuses 72 and 74. This effectively isolates the venous junction 70 and the superior sagittal sinus 56 with the operative region 90 of the catheter 10 disposed in the junction 70. Having at least partially inflated the balloons 38 and 41 by pressurizing the inflation lumen 105, perfusion of the venous junction 70 can begin.

Autologous oxygenated blood can be taken from any arterial source in the body. In the preferred embodiment, the blood pump 36 is connected to femoral artery 34 as discussed with reference to FIG. 1. This oxygenated blood is introduced into the connector 103 and through the associated perfusion lumen 101 to exit the catheter 10 through the ports 114–118 in the junction 70. Multiple port 114–118 are preferred in case one becomes blocked due to proximity to the vessel wall. The remaining ports will usually provide a clear passage.

At this point it is apparent that the oxygenated blood under pressure in the lumen 101 can escape through the distal hole 125 (FIG. 7) unless some provision is made for blocking that hole. This can be accomplished in several ways. For example, the guidewire 18 can be left in place so that it substantially fills the hole 125, thereby inhibiting the flow of oxygenated blood through the distal end 32 of the catheter 10. As noted, in a preferred method, the guidewire 18 is removed prior to the perfusion step, and the septum valve 127 automatically closes to block the distal hole 125.

As the perfusion of oxygenated blood begins, the junction 70 is pressurized to an extent that blood flow begins in the superior sagittal sinus 56 in a retrograde direction illustrated by the arrow 63. As noted with reference to FIG. 2, this retrograde flow perfuses the capillary bed 50 maintaining the tissue in a state of viability. A preferred range for the retrograde flow rate is between 50 and 250 milliliters per minute. This generally occurs with a range of pressures in the venous junction 70 of about 10 to 30 mm Hg.

There are several ways to control this pressure and flow rate at the junction 70. Gross pressure adjustments can be made at the blood pump 36 (FIG. 1). Minor adjustments in pressure can be made by inflating and deflating the balloons 38, 41 to adjust the degree of occlusion in the respective right and left transverse sinuses 72 and 74. If the balloons 38, 41 are deflated, the degree of occlusion is reduced, thereby permitting antegrade flow in the transverse sinuses 72, 74. As this antegrade flow is facilitated, the pressure in the junction 70 is reduced along with the retrograde flow in the superior sagittal sinus 56. In an embodiment wherein the catheter has three lumens as illustrated in FIG. 5, the balloons 38, 41 can be controlled simultaneously. In this case, a minor adjustment in the inflation pressure will have an effect in each of the transverse sinuses 72, 74.

An even finer degree of pressure control can be achieved with the four-lumen embodiment illustrated in FIG. 6. In this embodiment, the separate inflation lumens 132 and 134 permit separate control of the balloons 38 and 41, respectively. Thus, an adjustment of inflation pressure in only one of the lumens 132, 134 inflates or deflates only a single one of the balloons 38, 41, thereby permitting a finer degree of control over the pressure in the venous junction 70.

When the retroperfusion procedure is completed, the flow of oxygenated blood into the perfusion lumen 101 can be stopped, and the balloons 38, 41 can be deflated. With the catheter 10 in this low profile state, it can be withdrawn from the puncture site in the femoral vein 16. In an alternative method, wherein the guidewire 18 is left in place to block the distal hole 125, both the catheter 10 and guidewire 18 can be removed simultaneously.

In a preferred embodiment of the catheter 10, the tube 90 is formed from polyurethane. The balloons 38 and 41 can also be formed from polyurethane or some other elastomeric, compliant material. It would be apparent to those skilled in the art that many other types of materials will be more or less suited for a particular procedure.

It will also be apparent that there are many venous junctions within the body, each of which can be addressed in accordance with the apparatus and method disclosed above. Of course, the size and spacing of the balloons 38 and 41 may vary with a particular junction, and different retroperfusion rates and pressures may also be desired. In a conventional manner, the guidewire 18 may be replaced with or facilitated by a guide catheter. The number of perfusion ports 114–118 can also vary, it being appreciated that multiple ports are desirable in order to ensure that there are clear openings to the junction 70 if a particular port becomes blocked.

Given these wide variations in structure and method, which are all within the scope of this concept, one is cautioned not to restrict the invention to the embodiments which have been specifically disclosed and illustrated. Rather, the scope of the invention should be determined only with reference to the following claims.

We claim:

1. A catheter for a retroperfusing a venous junction defined by a first vein providing normal blood flow into the junction, and a second and third vein each providing normal blood flow away from the junction, the catheter comprising:
   an elongate tube having an axis extending between a proximal end and a distal end;
   portions of the tube defining a plurality of channels, including a through-lumen extending from the proximal end through the distal end of the tube;
   a first occlusion device disposed in proximity to the distal end of the tube and adapted to at least partially occlude the third vein;
   a second occlusion device disposed in proximity to the first occlusion device and adapted to at least partially occlude the second vein with the venous junction disposed between the first occlusion device and the second occlusion device; and
   a retroperfusion lumen included in the channels and having an outlet between the first occlusion device and the second occlusion device, the retroperfusion lumen being adapted to receive arterial blood or pharmacological agents under pressure in order to induce retrograde blood flow in the first vein.

2. The catheter recited in claim 1, further comprising:
   a pressure lumen included in the channels of the tube, the pressure lumen providing at the proximal end of the tube an indication of the fluid pressure at the venous junction.

3. The catheter recited in claim 2, further comprising:
   at least one radiopaque marker carried by the tube and having properties for facilitating placement of the first balloon relative to the venous junction.

4. The catheter recited in claim 3, further comprising:
   portions of the tube defining a first port providing fluid communication between the retroperfusion lumen and the venus junction; and
   portions of the tube defining at least one second port spaced from the first port and providing fluid communication between the retroperfusion lumen and the venus junction.

5. The catheter recited in claim 4, further comprising portions of the tube defining a soft tip distally of the first balloon.

6. The catheter recited in claim 5, further comprising:
   at least one inflation lumen included among the channels of the tube, the at least one inflation lumen providing fluid communication between the proximal end of the tube and at least one of the balloons, for at least partially inflating the at least one balloon in response to the fluid pressure at the venous junction.

7. A catheter combination for retroperfusing a venous junction defined by a first vein providing normal blood flow into the junction and a second and third vein each providing normal blood flow away from the junction, comprising:
   an elongate tube having an axis extending between a proximal end and a distal end;
   portions of the tube defining a plurality of channels including a through-lumen extending from the proximal end of the tube through the distal end of the tube;
   a first balloon disposed in proximity to the distal end of the tube and adapted to partially occlude the third vein;
   a second balloon disposed in proximity to the first balloon and adapted to partially occlude the second vein, the first balloon and the second balloon defining an operative region of the tube in proximity to the venous junction;
   a retroperfusion lumen included among the channels and adapted to provide fluid communication between the proximal end of the tube and the venous junction; and
   a blood pump providing a flow of arterial blood into the retroperfusion lumen at the proximal end of the tube, the pump having properties for pressurizing the flow of arterial blood at the venous junction so as to produce a retrograde flow of the blood in the first vein.

8. The catheter assembly recited in claim 7 further comprising:
   a pressure lumen included among the channels of the tube and extending between the proximal end of the tube and the operative region of the tube;
   portions of the tube defining at least one port in the operative region of the tube, the at least one port providing fluid communication between the retroperfusion lumen and the venous junction; and
   a pressure transducer disposed in fluid communication with the pressure lumen, the pressure transducer providing an indication of the fluid pressure at the venous junction.

9. The catheter assembly recited in claim 8, further comprising:
   at least one inflation lumen included among the channels and extending between the proximal end of the tube and the first balloon;
   an inflator providing fluid under pressure at the proximal end of the tube, the inflator being adapted to inflate and deflate the first balloon to control the occlusion of the third vein.

10. A method for retroperfusing a venous bed in the brain of a patient, the venous bed communicating with a venous junction defined by a first vein providing antegrade flow into the junction, and second and third veins providing antegrade blood flow away from the junction, the method comprising the steps of:

introducing into the second vein a catheter having a first balloon and a second balloon defining an operative region of the catheter, and a plurality of channels including a retroperfusion lumen exiting the catheter in the operative region, and an inflation lumen providing fluid communication with at least the first balloon;

positioning the catheter with the first balloon disposed in the third vein and the second balloon disposed in the second vein with the operative region of the catheter disposed in proximity to the venous junction;

pressurizing the retroperfusion lumen with arterial blood in order to provide an elevated blood pressure at the venous junction sufficient to induce retrograde blood flow in the first vein; and pressurizing the inflation lumen with a fluid to inflate at least the first balloon in order to control the antegrade blood flow from the venous junction.

11. The method recited in claim 10 further comprising the steps of:

providing a pressure lumen in the catheter;

placing a pressure transducer in fluid communication with the pressure lumen, the transducer providing an indication of pressure at the venous junction; and during the second pressurizing step, monitoring the indication of the pressure transducer to control the antegrade blood flow from the venous junction.

12. The method recited in claim 11 wherein the controlling step further comprises the step of independently controlling the inflation of the first balloon and the second balloon in response to the indication of the pressure transducer.

* * * * *